(12) United States Patent
Kleyman

(10) Patent No.: US 10,772,661 B2
(45) Date of Patent: Sep. 15, 2020

(54) METHOD AND STRUCTURE FOR SELECTIVELY LOCKING PORTIONS OF A SEAL ASSEMBLY

(71) Applicant: Covidien LP, Mansfield, MA (US)

(72) Inventor: Gennady Kleyman, Brooklyn, NY (US)

(73) Assignee: COVIDIEN LP, Mansfield, MA (US)

( * ) Notice: Subject to any disclaimer, the term of this patent is extended or adjusted under 35 U.S.C. 154(b) by 132 days.

(21) Appl. No.: 16/152,562

(22) Filed: Oct. 5, 2018

(65) Prior Publication Data

US 2019/0029720 A1    Jan. 31, 2019

Related U.S. Application Data

(63) Continuation of application No. 15/875,480, filed on Jan. 19, 2018, now Pat. No. 10,111,685, which is a continuation of application No. 15/002,832, filed on Jan. 21, 2016, now Pat. No. 9,895,164, which is a continuation of application No. 13/933,344, filed on Jul. 2, 2013, now Pat. No. 9,247,956.

(60) Provisional application No. 61/673,390, filed on Jul. 19, 2012.

(51) Int. Cl.
*A61B 17/34* (2006.01)
*A61B 17/02* (2006.01)
*A61B 17/00* (2006.01)

(52) U.S. Cl.
CPC ...... *A61B 17/3423* (2013.01); *A61B 17/0218* (2013.01); *A61B 17/3462* (2013.01); *A61B 17/3498* (2013.01); *A61B 2017/00477* (2013.01)

(58) Field of Classification Search
CPC .............. A61B 17/064; A61B 17/0642; A61B 2017/000526; A61B 17/3462; A61B 17/0218
See application file for complete search history.

(56) References Cited

U.S. PATENT DOCUMENTS

| 4,402,683 A | 9/1983 | Kopman |
| 5,290,245 A | 3/1994 | Dennis |
| 5,366,478 A | 11/1994 | Brinkerhoff et al. |
| 5,385,552 A | 1/1995 | Haber et al. |
| 5,514,133 A | 5/1996 | Golub et al. |
| 5,520,610 A | 5/1996 | Giglio et al. |
| 5,524,501 A | 6/1996 | Patterson et al. |

(Continued)

OTHER PUBLICATIONS

European Search Report for counterpart EP Application No. EP13177088, dated Aug. 20, 2014, 7 pages.

*Primary Examiner* — Christian A Sevilla
(74) *Attorney, Agent, or Firm* — Carter, DeLuca & Farrell LLP

(57) ABSTRACT

A surgical access device that includes a seal assembly. The seal assembly includes an upper housing portion having a first seal and a lower housing portion including a second seal. The upper housing portion is rotatably connectable to the lower housing portion. The surgical access device also includes a rotation prevention mechanism configured to prevent inadvertent relative rotation of, and disconnection of, the upper housing portion and the lower housing portion. The rotation prevention mechanism is further configured to be selectively actuated by a user, such that, when actuated, the upper housing portion is selectively rotatable relative to, and disconnectable from, the lower housing portion.

17 Claims, 11 Drawing Sheets

(56) References Cited

U.S. PATENT DOCUMENTS

| | | |
|---|---|---|
| 5,538,509 A | 7/1996 | Dunlap et al. |
| 5,549,565 A | 8/1996 | Ryan et al. |
| 5,569,205 A | 10/1996 | Hart et al. |
| 5,672,168 A | 9/1997 | de la Torre et al. |
| 5,720,730 A | 2/1998 | Blake, III |
| 5,792,113 A | 8/1998 | Kramer et al. |
| 5,800,451 A | 9/1998 | Buess et al. |
| 5,871,471 A | 2/1999 | Ryan et al. |
| 5,957,927 A | 9/1999 | Magee et al. |
| 6,093,176 A | 7/2000 | Dennis |
| 6,482,181 B1 | 11/2002 | Racenet et al. |
| 6,485,467 B1 | 11/2002 | Crook et al. |
| 6,613,038 B2 | 9/2003 | Bonutti et al. |
| 6,702,787 B2 | 3/2004 | Racenet et al. |
| 6,740,064 B1 | 5/2004 | Sorrentino et al. |
| 6,811,546 B1 | 11/2004 | Callas et al. |
| 7,276,075 B1 | 10/2007 | Callas et al. |
| 7,393,322 B2 | 7/2008 | Wenchell |
| 7,678,046 B2 | 3/2010 | White et al. |
| 7,744,569 B2 | 6/2010 | Smith |
| 7,918,827 B2 | 4/2011 | Smith |
| 7,931,624 B2 | 4/2011 | Smith et al. |
| 8,002,750 B2 | 8/2011 | Smith |
| 8,002,786 B2 | 8/2011 | Beckman et al. |
| 8,012,128 B2 | 9/2011 | Franer et al. |
| 8,029,475 B2 | 10/2011 | Franer et al. |
| 8,092,431 B2 | 1/2012 | Lunn et al. |
| 8,109,873 B2 | 2/2012 | Albrecht et al. |
| 8,118,735 B2 | 2/2012 | Voegele |
| 8,206,411 B2 | 6/2012 | Thompson et al. |
| 8,597,180 B2 | 12/2013 | Copeland et al. |
| 8,961,406 B2 | 2/2015 | Ortiz et al. |
| 9,247,956 B2 | 2/2016 | Kleyman |
| 9,895,164 B2 | 2/2018 | Kleyman |
| 10,111,685 B2 | 10/2018 | Kleyman |
| 2002/0091410 A1 | 7/2002 | Ben-David et al. |
| 2002/0173748 A1 | 11/2002 | McConnell et al. |
| 2004/0054353 A1 | 3/2004 | Taylor |
| 2004/0073090 A1 | 4/2004 | Butler et al. |
| 2004/0204682 A1 | 10/2004 | Smith |
| 2005/0033342 A1 | 2/2005 | Hart et al. |
| 2005/0070851 A1* | 3/2005 | Thompson ......... A61B 17/3462 604/167.03 |
| 2005/0070946 A1 | 3/2005 | Franer et al. |
| 2005/0192594 A1 | 9/2005 | Skakoon et al. |
| 2005/0209608 A1 | 9/2005 | O'Heeron |
| 2005/0212221 A1 | 9/2005 | Smith et al. |
| 2005/0222582 A1* | 10/2005 | Wenchell ........... A61B 17/3423 606/108 |
| 2006/0020281 A1 | 1/2006 | Smith |
| 2006/0211992 A1 | 9/2006 | Prosek |
| 2006/0217665 A1 | 9/2006 | Prosek |
| 2006/0224120 A1 | 10/2006 | Smith et al. |
| 2007/0088277 A1 | 4/2007 | McGinley et al. |
| 2007/0185453 A1 | 8/2007 | Michael et al. |
| 2008/0051739 A1 | 2/2008 | McFarlane |
| 2008/0146884 A1 | 6/2008 | Beckman et al. |
| 2008/0208222 A1 | 8/2008 | Beckman et al. |
| 2010/0228096 A1 | 9/2010 | Weisenburgh, II et al. |
| 2010/0261975 A1* | 10/2010 | Huey ................. A61B 17/3423 600/208 |
| 2011/0118833 A1 | 5/2011 | Reichenbach et al. |
| 2015/0065808 A1 | 3/2015 | Van Wyk et al. |

* cited by examiner

METHOD AND STRUCTURE FOR SELECTIVELY LOCKING PORTIONS OF A SEAL ASSEMBLY

CROSS-REFERENCE TO RELATED APPLICATIONS

The present application is a continuation of U.S. patent application Ser. No. 15/875,480, filed Jan. 19, 2018, which is a continuation of U.S. patent application Ser. No. 15/002,832, filed Jan. 21, 2016, now U.S. Pat. No. 9,895,164, which is a continuation of U.S. patent application Ser. No. 13/933,344, filed Jul. 2, 2013, now U.S. Pat. No. 9,247,956, which claims the benefit of U.S. Provisional Patent Application Ser. No. 61/673,390, filed on Jul. 19, 2012, the entire disclosure of each of which is incorporated by reference herein.

TECHNICAL FIELD

The present disclosure relates to a surgical device and, more particularly, but not exclusively, relates to a mechanism for selectively locking portions of a seal assembly relative to each other.

BACKGROUND

Minimally invasive and laparoscopic procedures generally require that any instrumentation inserted into the body is sealed, e.g., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere. In view of the need to maintain the atmospheric integrity of the inner area of the cavity, a seal assembly for a cannula, which permits introduction of a wide range of surgical instrumentation and maintains the atmospheric integrity of the inner area of the cavity is desirable.

SUMMARY

The present invention, in accordance with various embodiments thereof, may be directed to a surgical access device comprising: a seal assembly including an upper housing portion having a first seal and a lower housing portion including a second seal, the upper housing portion being rotatably connectable to the lower housing portion; and a rotation prevention mechanism configured to prevent inadvertent relative rotation, and disconnection, the upper housing portion and the lower housing portion, the rotation prevention mechanism further configured to be selectively actuated by a user, such that, when actuated, the upper housing portion is selectively rotatable relative to, and disconnectable from, the lower housing portion.

The rotation prevention mechanism may include components that are integrally formed with one or both of the upper housing portion and the lower housing portion. The rotation prevention mechanism may include components that are integrally formed with other components that are fixedly connected to one or both of the upper housing portion and the lower housing portion. The rotation prevention mechanism may include a first component that is integrally formed with the upper housing portion and a second component that is fixedly connected to the lower housing portion.

In an example embodiment, the first component may comprise a finger. The finger may be integrally formed with a circumferential edge of a main housing, the main housing being fixedly connected to lower housing portion. The finger may include a ramp located on its upper surface. The second component of the rotation prevention mechanism may include a protrusion, the protrusion being integrally formed with a circumferential edge of upper housing portion and including a distal-extending member. The finger may be configured for resilient movement relative to the main housing about its point of attachment thereto, such that at least a portion of the finger is moveable distally relative to the main housing.

In an embodiment, as the upper housing portion of the seal assembly is rotated in a first direction, the distal-extending member of the protrusion travels up the sloping surface of the ramp and exerts a force on the finger sufficient to cause the finger to move distally relative to the main housing until, when the distal-extending member of the protrusion reaches the end of the sloping surface of the ramp, the force exerted on the ramp by the distal-extending member of the protrusion is removed, and the finger, by virtue of its resilience, is allowed to move proximally to a position in which the distal-extending member of the protrusion is distal relative to the uppermost point of the ramp, thereby preventing the upper housing portion from rotating in a second direction opposite to the first direction.

In an embodiment, upon a user exerting a force on the finger, the finger is moveable distally relative to the main housing until the uppermost point of the ramp is located distal relative to the distal-extending member of the protrusion such that the upper housing portion of the seal assembly is not prevented from rotating, but rather is free to rotate, in the second direction relative to the lower housing portion.

BRIEF DESCRIPTION OF THE DRAWINGS

The foregoing features of the present disclosure will become more readily apparent and will be better understood by referring to the following detailed description of various embodiments, which are described hereinbelow with reference to the drawings wherein.

Figure 1:
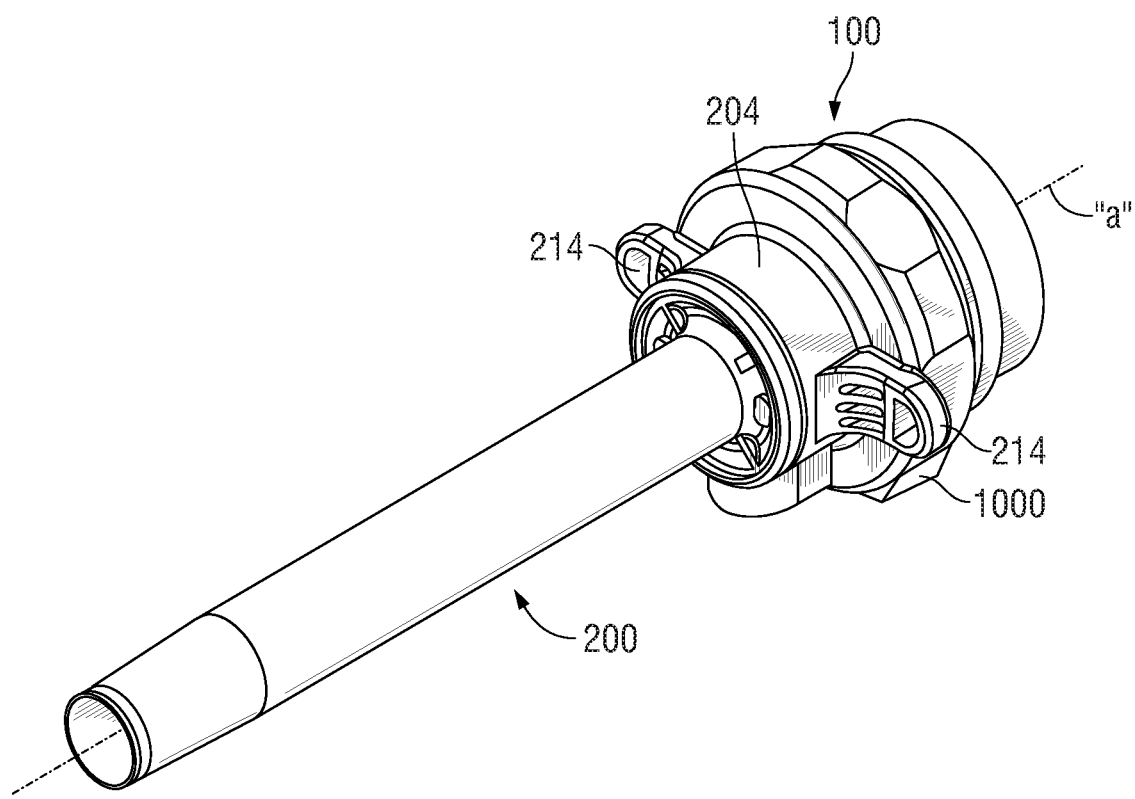
FIGS. 1-2 are perspective views of a cannula assembly and a seal assembly in accordance with an example embodiment of the present disclosure.

The figures depict various embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

As set forth above, the present invention, in accordance with various embodiments thereof, may be directed to an arrangement for preventing a rotatably connectable upper housing portion of a seal housing from inadvertently rotating relative to a lower housing portion of the seal housing during use and thereby undesirably disconnecting therefrom. In this regard, the present invention, in accordance with various embodiments thereof, may also be directed to an arrangement which provides a selectively actuatable mechanism that enables a user, e.g., a surgeon, upon actuation, to rotate an upper housing portion of a seal housing that is connected to lower housing portion of the seal housing and thereby disconnect the two portions from each other. By providing a selectively actuatable mechanism that i) when in a first position, automatically prevents a rotatably connectable upper housing portion of a seal housing from inadvertently rotating relative to a lower housing portion of the seal housing during use, and that ii) when actuated, enables a user to rotate and thereby disconnect the upper housing portion from lower housing portion of the seal housing, various advantages may be achieved, as will be set for the ion greater detail below.

It should be noted that the seal assembly set forth herein, e.g., a gimbal seal, is merely one example of a seal arrangement that may be employed in the present invention. Any type of seal arrangement may be employed and still be within the scope of the present invention. In the example shown herein, the seal assembly, either alone or in combination with a seal system internal to a cannula assembly, provides a substantial seal between a body cavity of a patient and the outside atmosphere before, during and after insertion of an instrument through the cannula assembly. Moreover, the seal assembly of the present invention is advantageously capable of accommodating instruments of varying diameters, e.g., from 5 mm to 15 mm, by providing a gas tight seal with each instrument when inserted. The flexibility of the present seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the seal assembly accommodates angular manipulation of the surgical instrument relative to the seal axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laproscopes, tubes, and the like. Such instruments will be collectively referred to herein as "instruments or instrumentation".

In the following description, as is traditional the term "proximal" refers to the portion of the instrument closest to the operator while the term "distal" refers to the portion of the instrument remote from the operator.

Figure 2:
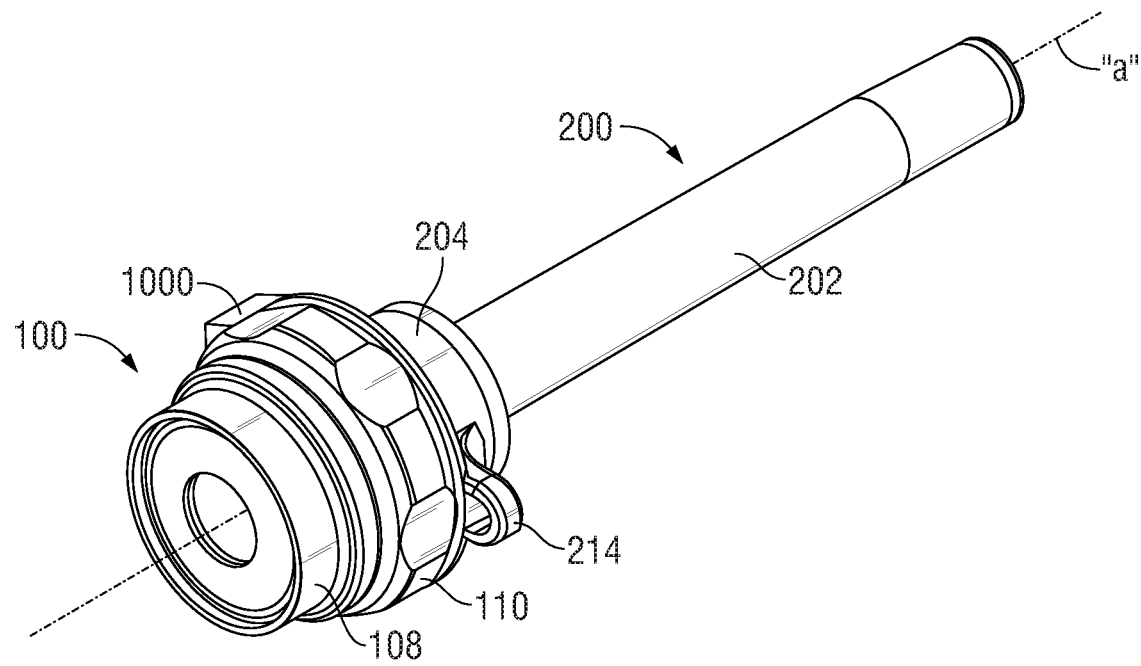

Referring now to the drawings, in which like reference numerals identify identical or substantially similar parts throughout the several views, FIGS. 1-2 illustrate the seal assembly 100 of the present disclosure mounted to cannula assembly 200. Cannula assembly 200 may be any conventional cannula suitable for the intended purpose of accessing a body cavity and permit introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which is an instrument positionable within the passageway of the cannula assembly 200. The obturator assembly is utilized to penetrate the abdominal wall and then subsequently removed from the cannula assembly to permit introduction of the surgical instrumentation utilized to perform the procedure.

Cannula assembly 200 includes cannula sleeve 202 and cannula housing 204 mounted to an end of the sleeve 202. Cannula sleeve 202 defines a longitudinal axis "a" extending along the length of sleeve 202. Sleeve 202 further defines an internal longitudinal passage dimensioned to permit passage of surgical instrumentation. Sleeve 202 may be formed of stainless steel or other rigid materials such as a polymeric material or the like. Sleeve 202 may be clear or opaque. The diameter of sleeve 202 may vary, but typically ranges from 10 to 15 mm for use with the seal assembly 100 of the present disclosure.

Figure 3:
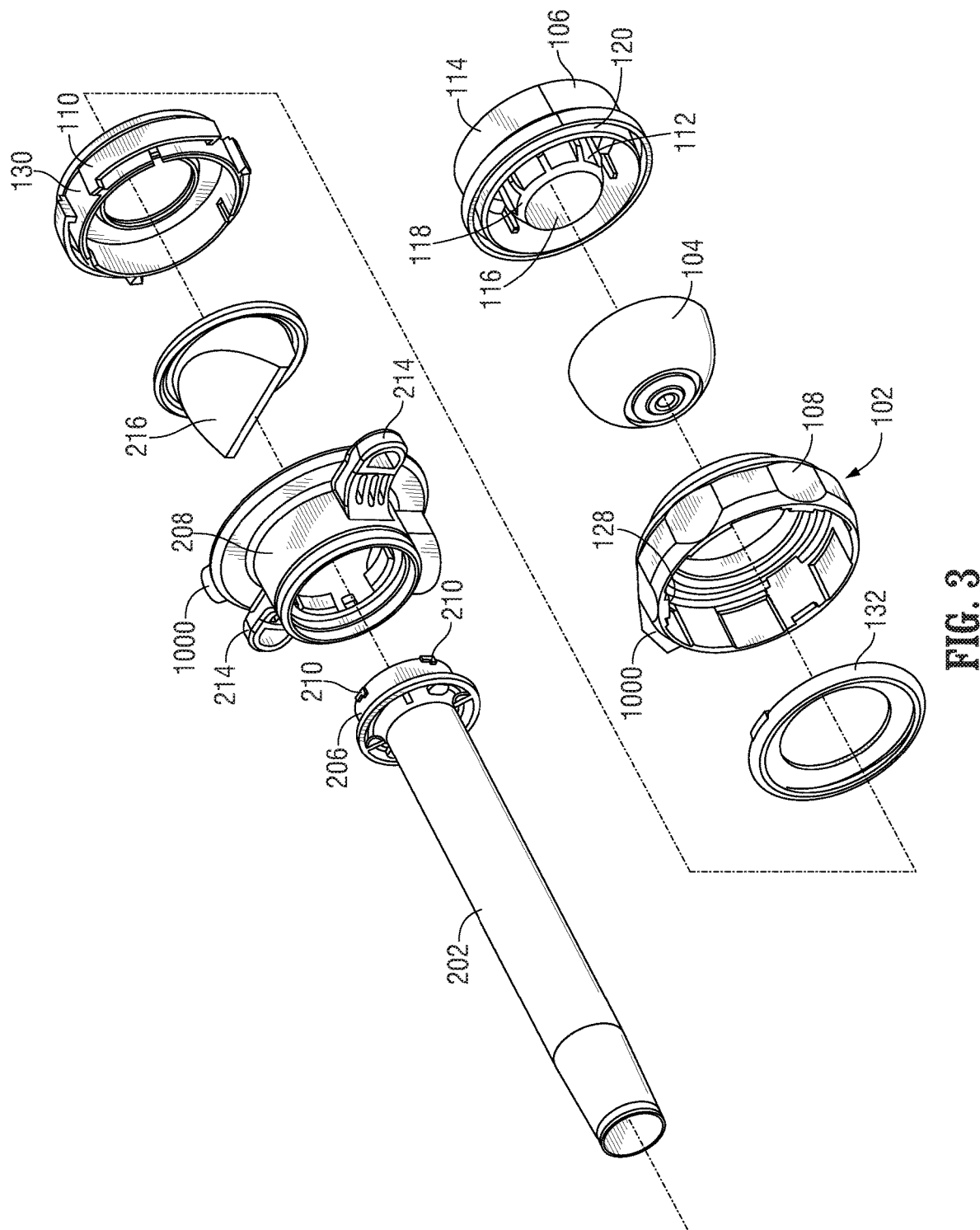
FIG. 3 is a perspective view with parts separated of the cannula and seal assemblies of FIG. 1.
Figure 4:
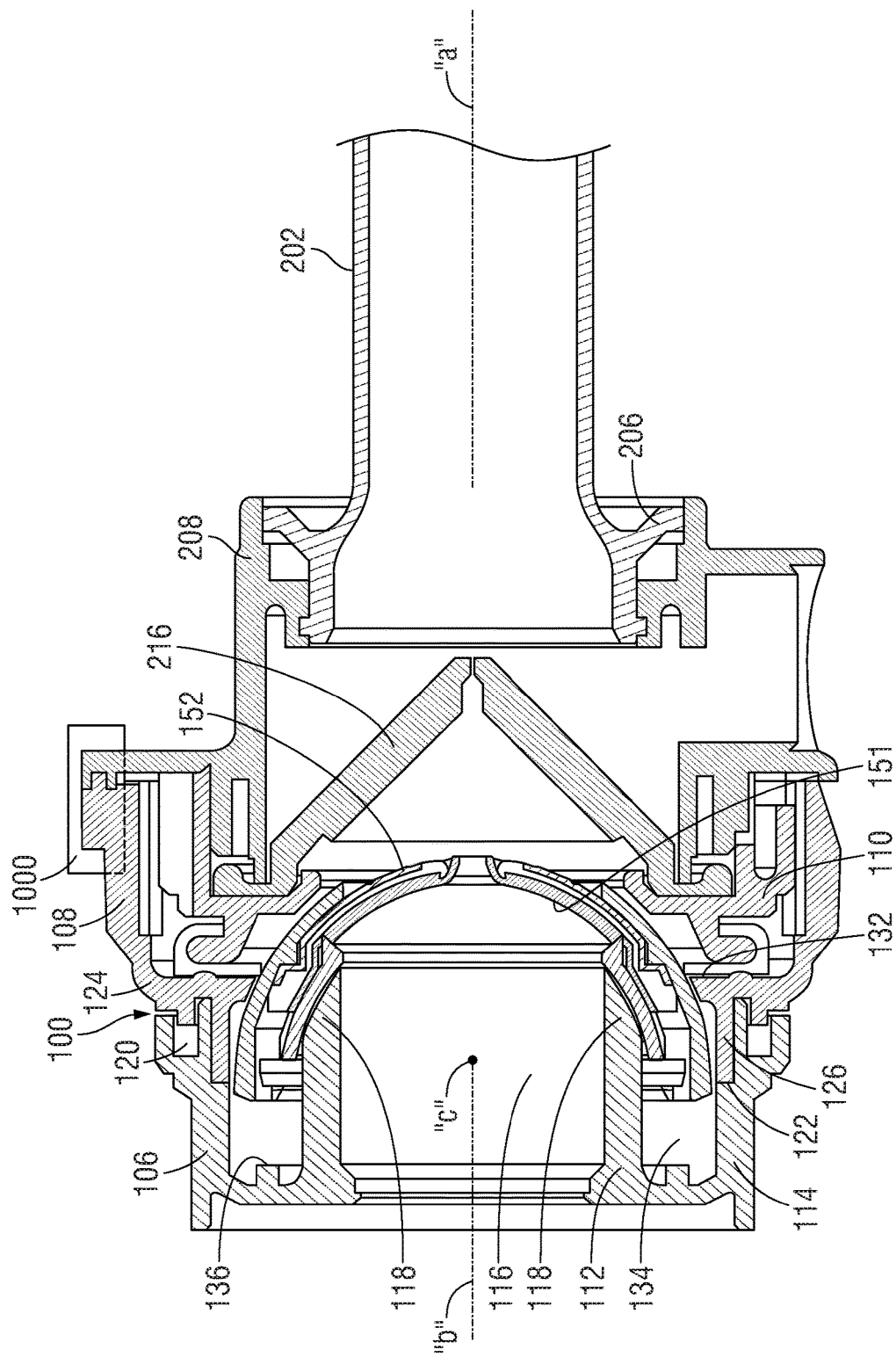
FIG. 4 is a side cross-sectional view of the cannula and seal assemblies.
Figure 7:
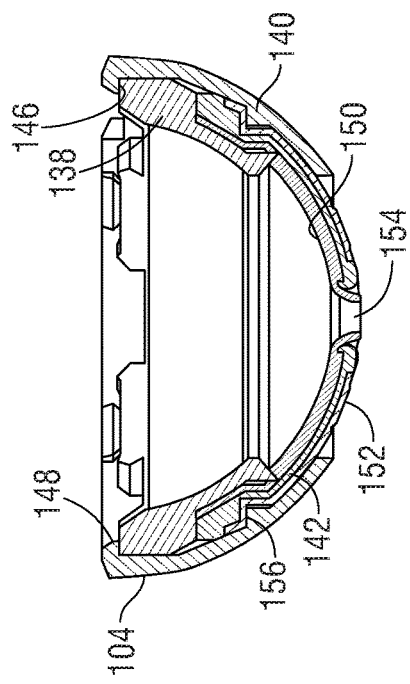
FIGS. 7-8 are cross-sectional views of the gimbal mount.
Figure 8:
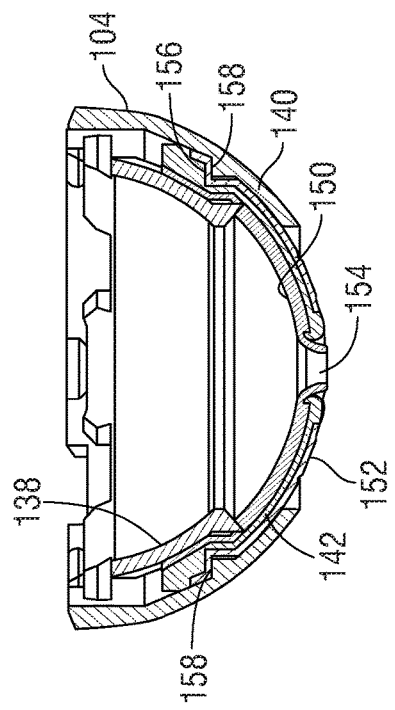
Figure 5:
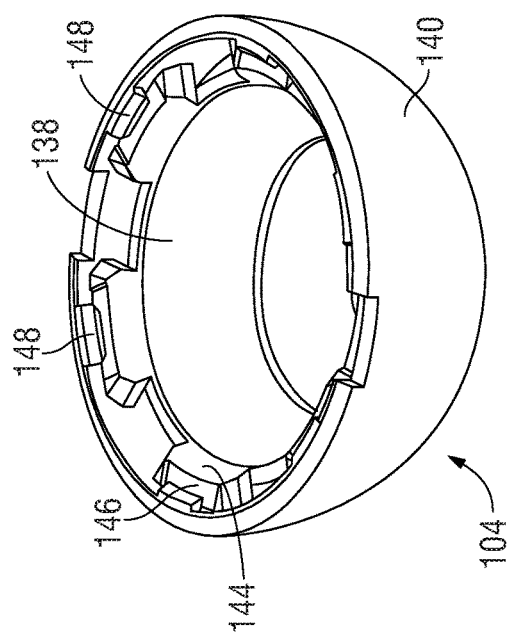
FIGS. 5-6 are top and bottom perspective views of a gimbal mount of the seal assembly.

Cannula housing 204 includes two components, specifically, housing flange 206 which is attached to the proximal end of cannula sleeve 202 and main housing 208 as shown in FIGS. 3-4. Main housing 208 is connectable to housing flange 206 through a bayonet coupling consisting of radially spaced tongues 210 on the exterior of housing flange 206 and corresponding recesses 212 within the interior of main housing 208. Tongues 210 are receivable within recesses 212. Thereafter, housing flange 206 and main housing 208 are rotated to securely lock the tongues 210 within the recesses 212. Other conventional means, e.g., a snap fit, ultrasonic welding or any other means envisioned by one skilled in the art including, e.g., adhesive means, may be incorporated to connect housing flange 206 and main housing 208. Main housing 208 further includes diametrically opposed housing grips 214 dimensioned and arranged for gripping engagement by the fingers of the user. Although shown and described as two components, cannula housing 204 may be a single component and attached to cannula sleeve 202 by any of the aforementioned means.

With reference to FIG. 3, in conjunction with FIGS. 1-2, cannula housing 204 further includes duck bill or zero closure valve 216 which tapers distally and inwardly to a sealed configuration as shown in the figure. Valve 216 opens to permit passage of the surgical instrumentation and closes in the absence of the instrumentation. Valve 216 is preferably adapted to close upon exposure to the forces exerted by the insufflation gases in the internal cavity. Other zero closure valves are also contemplated including single or multiple slit valve arrangements, trumpet valves, flapper valves, etc.

Referring now to FIGS. 3-4, in conjunction with FIGS. 1-2, seal assembly 100 will be discussed in detail. Seal assembly 100 includes seal housing, generally identified as reference numeral 102, and gimbal mount 104 which is disposed within the seal housing 102. Seal housing 102 houses the sealing components of the assembly and defines the outer valve or seal body of the seal assembly 100. Seal housing 102 defines central seal housing axis "b" which is preferably parallel to the axis "a" of cannula sleeve 202 and, more specifically, coincident with the axis "a" of the cannula. Seal housing 102 incorporates three housing components, namely, proximal, distal and inner housing components 106, 108, 110, respectively, which, when assembled together, form the seal housing 102. Assembly of housing components 106, 108, 110 may be affected by any of the aforementioned connection means discussed with respect to cannula housing 204. Further, seal housing 102 may be considered as having an upper housing portion 109 formed by components 106 108, as shown separately in FIGS. 10-12, and a detachable lower housing portion formed by component 110.

Proximal housing component 106 defines inner guide wall 112 and outer wall 114 disposed radially outwardly of the inner guide wall 112. Inner guide wall 112 defines central passage 116 which is dimensioned to receive a surgical instrument and laterally confine the instrument within seal housing 102. Inner guide wall 112 is generally cylindrical in configuration and terminates in a distal arcuate surface 118. Outer wall 114 defines first and second annular recesses 120, 122 adjacent its distal end. Recesses 120, 122 receive corresponding structure, e.g., annular lips 124, 126 of distal housing component 108 to facilitate connection of the two components. As appreciated, proximal housing component 106 may also incorporate locking tabs which engage corresponding structure of distal housing component 108 upon relative rotation of the components 106, 108 to securely connect the components.

Inner housing component 110 is disposed within the interior of distal housing component 108 and is connectable to the distal housing component 108 through a bayonet coupling. Such coupling includes radially spaced tongues 128 which depend radially inwardly to be received within correspondingly arranged grooves or recesses 130 on the exterior of inner housing component 110. Coupling of distal and inner housing components 108, 110, and thus coupling of upper housing portion 109 and lower housing portion 110, is thereby affected through rotation of the components. In order to prevent inadvertent relative rotation, and thus potential decoupling, of upper housing portion 109 and lower housing portion 110, the present invention, in accordance with various example embodiments thereof, may include a rotation prevention mechanism 1000, shown schematically in, e.g., FIGS. 1-4 and 13. Further details of a specific example of such a rotation prevention mechanism 1000 are shown, e.g., in FIGS. 15-17.

In general, the rotation prevention mechanism 1000 is a mechanism that may prevent inadvertent relative rotation, and thus potential decoupling, of upper housing portion 109 and lower housing portion 110. In addition, the rotation prevention mechanism 1000 is a mechanism that may enable a user, e.g., a surgeon, upon actuation, to selectively rotate an upper housing portion of a seal housing relative to a lower housing portion of the seal housing and thereby selectively disconnect the two portions from each other. The rotation prevention mechanism 1000 may include components that are separate from the seal assembly 100 and/or the cannula assembly 200, but preferably include components that are integrally formed with one or more components of either the seal assembly 100 and/or the cannula assembly 200. In an embodiment, the rotation prevention mechanism 1000 may include components that are integrally formed with one or both of the upper housing portion of a seal housing and the lower housing portion of the seal housing. Additionally or alternatively, the rotation prevention mechanism 1000 may include components that are integrally formed with components that are fixedly connected to one or both of the upper housing portion and the lower housing portion of the seal housing.

Figure 15:
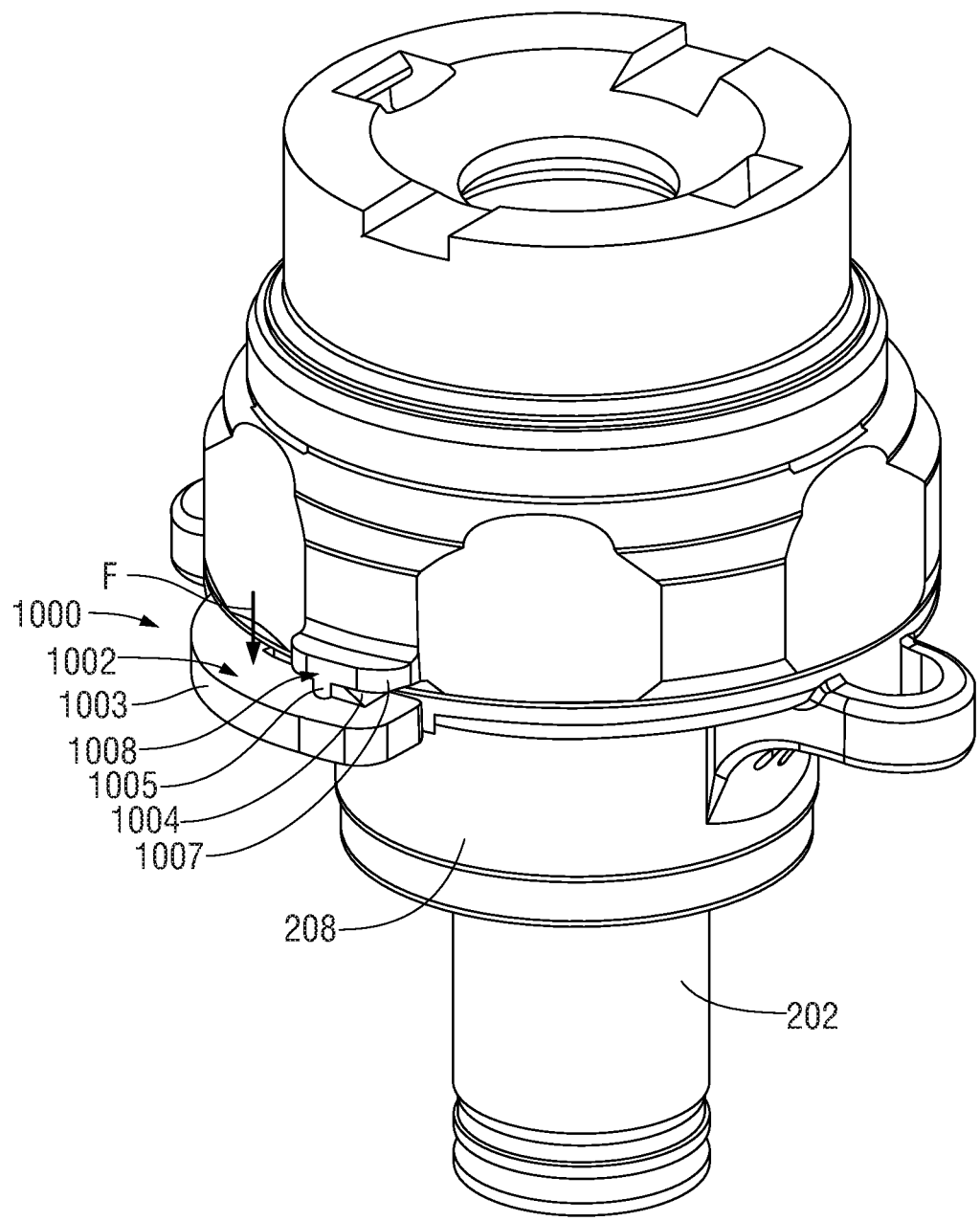
FIGS. 15-17 are perspective views of an example embodiment of a mechanism for preventing inadvertent rotation, and potential inadvertent disconnection, of an upper housing portion and a lower housing portion of a seal assembly.
Figure 16:
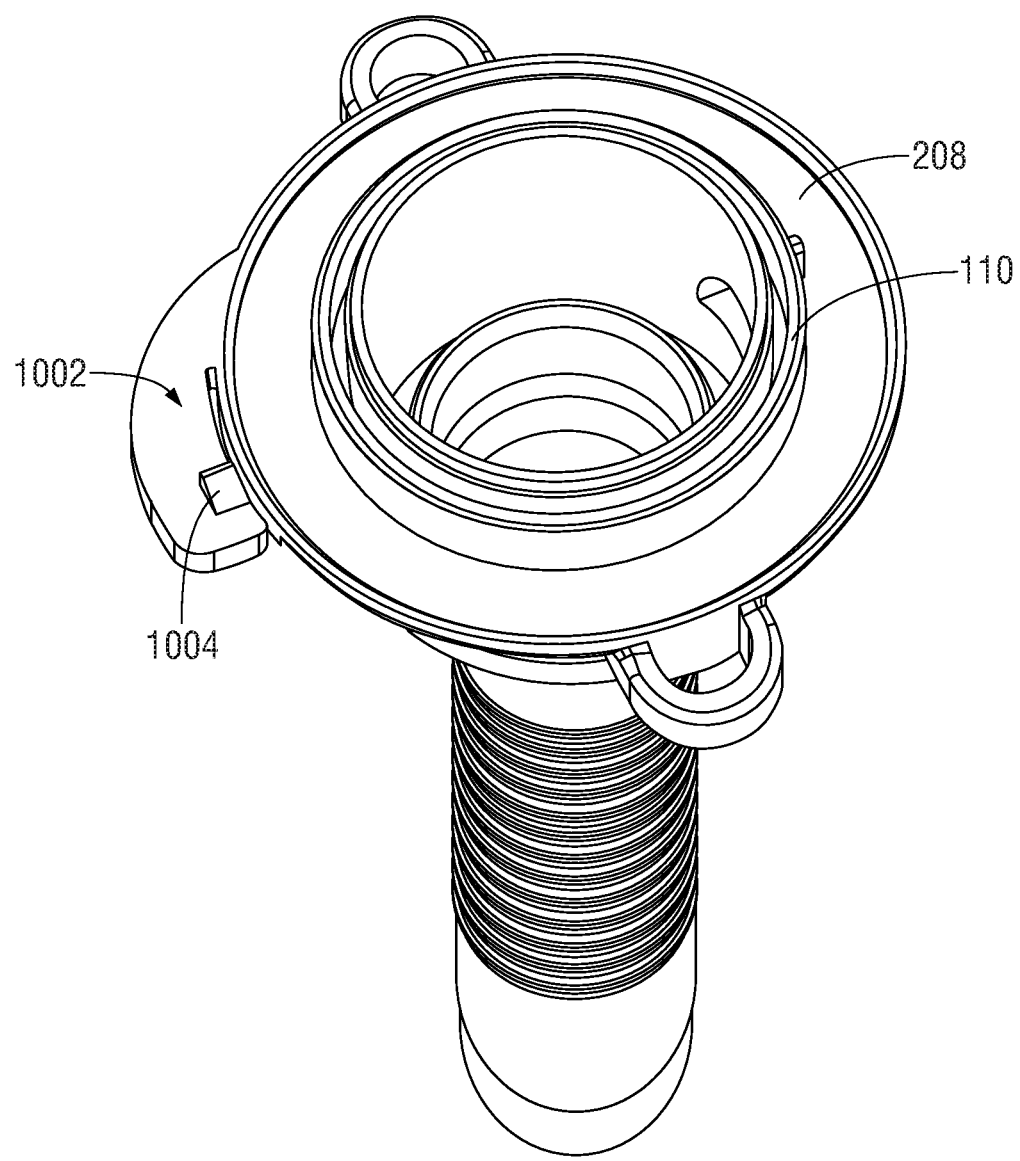
Figure 17:
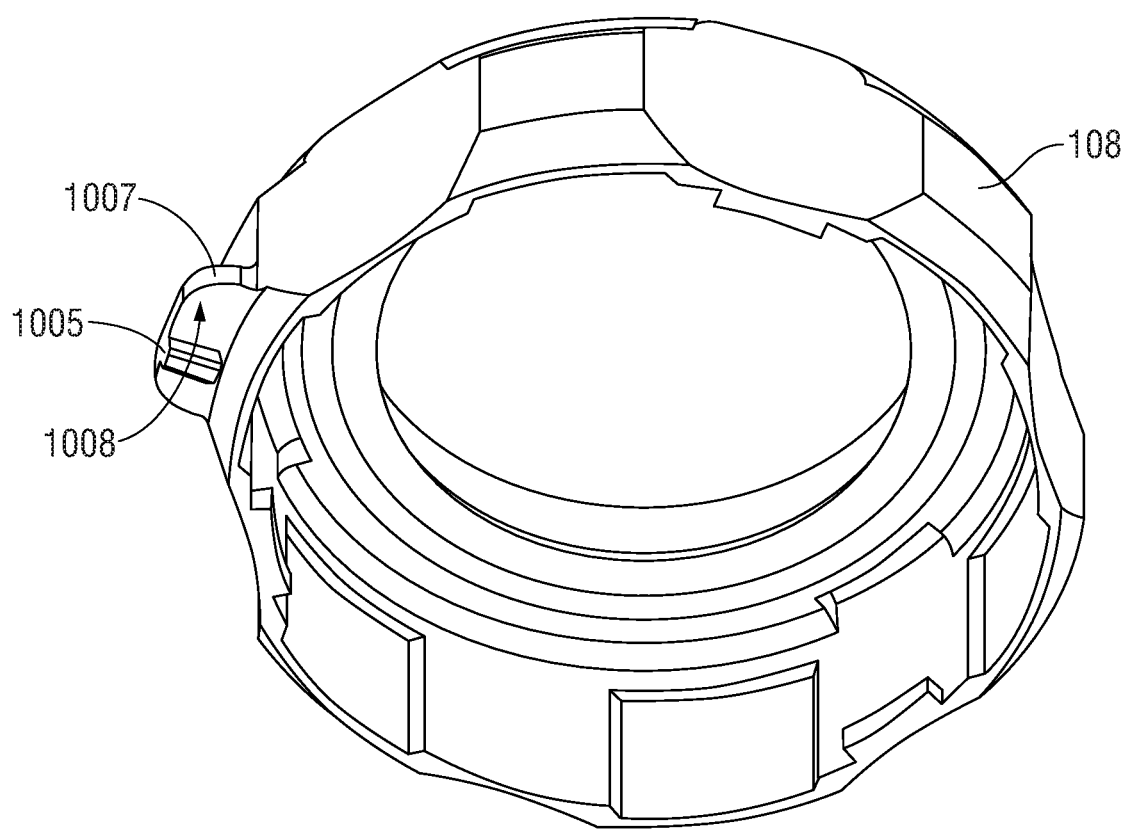

The embodiment shown and described herein provides an example of this latter arrangement. Specifically, the embodiment shown and described herein in FIGS. 15-17 provides an example of the rotation prevention mechanism 1000 which includes a first component that is integrally formed with the upper housing portion 109 and a second component that is fixedly connected to the lower housing portion 110 of the seal housing 102. Alternate embodiments may include different arrangements, e.g., wherein the rotation prevention mechanism 1000 includes components that are integrally formed with different components that are fixedly connected to either the upper housing portion 109 and/or the lower housing portion 110 of the seal housing 102. It should also be recognized that, while the example embodiment shown and discussed herein provides for an arrangement in which the rotation prevention mechanism 1000 includes, e.g., two, components, other embodiments are envisioned in which the rotation prevention mechanism 1000 includes only one component (e.g., a component that is part of or connected to a single one of the upper housing portion 109 and/or the lower housing portion 110 of the seal housing 102), or includes more than two components (e.g., components that are part of or connected to other components in addition to the upper housing portion 109 and the lower housing portion 110 of the seal housing 102).

Referring now to FIGS. 15-17, there is shown an example embodiment of the present invention. In this embodiment, as mentioned previously, there is provided an example of the rotation prevention mechanism 1000 which includes a first component 1002 and a second component 1008. As shown, the first component 1002 consists of a finger 1003 that is integrally formed with a circumferential edge of the main housing 208, the finger having a ramp 1004 located on its upper surface. It is noted that the main housing 208, in this embodiment, is fixedly connected to lower housing portion 110. In addition, as shown in this embodiment, the second component 1008 of the rotation prevention mechanism 1000 is a protrusion 1007 that is integrally formed with a circumferential edge of the distal housing component 108 of the upper housing portion 109 of the seal housing 102. In addition, the protrusion 1007 includes a distal-extending member 1005. The finger 1003 is configured for resilient movement relative to the main housing 208 about its point of attachment thereto, such that at least a portion of the finger, e.g., the portion including the ramp 1004, is moveable distally relative to the main housing 208. In this way, as the upper housing portion 109 of the seal assembly is rotated in a first direction (e.g., clockwise when FIG. 15 is viewed from above), the distal-extending member 1005 of the protrusion 1007 travels up the sloping surface of the ramp 1004 until it reaches the end of the sloping surface. As the distal-extending member 1005 of the protrusion 1007 travels up the sloping surface of the ramp 1004, it exerts a force, e.g., a force directed in the distal direction, on the ramp 1004, and thus also on the finger 1003, the distally-directed force being sufficient to cause the finger 1003 to move distally relative to the main housing 208 about its point of attachment thereto. Once the distal-extending member 1005 of the protrusion 1007 reaches the end of the sloping surface of the ramp 1004, the distally-directed force exerted on the ramp 1004 by the distal-extending member 1005 of the protrusion 1007 is removed, and the finger 1003, by virtue of its resilience, is allowed to move proximally, thereby returning to its original position relative to the main housing 208 (e.g., its position prior to being moved by the force exerted by the distal-extending member 1005 of the protrusion 1007). In this original position, the distal-extending member 1005 of the protrusion 1007 extends to a position that is distal relative to the uppermost point of the ramp, and thus the upper housing portion 109 of the seal assembly is prevented from rotating in a second direction (e.g., counter-clockwise when FIG. 15 is viewed from above) opposite to the first direction. In this manner, the rotation prevention mechanism 1000 automatically prevents the upper housing portion 109 of the seal housing 102 from inadvertently rotating relative to, and thus inadvertently becoming disconnected from, the lower housing portion 110 once the upper housing portion 109 of the seal housing 102 reaches this locked position.

Once a user determines that it would be desirable to disconnect and/or remove the upper housing portion 109 of the seal housing 102 from the lower housing portion 110, the user may then exert a force, e.g., a force directed in the distal direction, on the finger 1003. This distally-directed force may be sufficient to cause the finger 1003 to move distally relative to the main housing 208 about its point of attachment thereto until the uppermost point of the ramp 1004 is located distal relative to the distal-extending member 1005 of the protrusion 1007 of the upper housing portion 110. In this position, the upper housing portion 109 of the seal assembly is no longer prevented from rotating, but rather is free to rotate, in the second direction (e.g., counter-clockwise when FIG. 15 is viewed from above) relative to the lower housing portion 110. In this manner, the rotation prevention mechanism 1000 provides a selectively actuatable mechanism that, when actuated, enables a user to rotate and thereby disconnect an upper housing portion from a lower housing portion of the seal housing.

With continued reference to FIGS. 3 and 4, seal assembly 100 further includes skirt seal 132 mounted about the proximal end of inner housing component 110 or on the upper surface of the inner housing component 110 (constituting a lower component) of the seal housing 102. Skirt seal 132 functions in minimizing the loss of insufflation gases through seal housing 102. Skirt seal 132 also engages gimbal mount 104 and serves to bias the gimbal mount in a proximal direction against inner guide wall 112 of proximal housing 106 as will be discussed. Skirt seal 132 is preferably fabricated from a suitable elastomeric material or the like to provide a spring-like characteristic sufficient to appropriately bias gimbal mount 104.

With particular reference to FIG. 4, gimbal mount 104 is accommodated within an annular space 134 defined between inner and outer walls 112, 114 of proximal housing component 106. Gimbal mount 104 is mounted in a manner which permits angulation of the gimbal mount 104 relative to seal axis "b". Specifically, gimbal mount 104 is free to angulate about an axis or center of rotation "c" through a range of motion defined within the confines of annular space 134. An annular stop 136 may extend within annular space 134. Annular stop 136 is positioned to limit the degree of angulation of gimbal mount 104 if desired. The range of movement of gimbal mount 104 will be discussed in greater detail hereinbelow.

Referring now to FIGS. 5-9, in conjunction with FIG. 4, the components of gimbal mount 104 will be discussed in further detail. Gimbal mount 104 includes first and second gimbal housings 138, 140 and resilient seal member 142 which is mounted between the housings 138, 140. In a preferred arrangement, first and second gimbal housings 138, 140 and seal member 142 each define a general hemispherical configuration as shown. First gimbal housing 138 is preferably seated within second gimbal housing 140 and secured to the second gimbal housing 140 through a snap fit connection or the like. Preferably, first gimbal housing 138 includes a plurality of mounting legs 144 radially spaced about the outer periphery of the housing component 138. Legs 144 define locking surfaces 146 which extend in general transverse relation to the axis "b" of seal assembly 200. Similarly, second gimbal housing 140 includes a plurality of corresponding locking detents 148 spaced about the interior of the housing 140. Upon insertion of first gimbal housing 138 within second gimbal housing 140, mounting legs 144 slide along locking detents 148 whereby upon clearing the detents 148, locking surfaces 146 of the mounting legs 146 securely engage the locking detents 148 to fix first gimbal housing 138 within second gimbal housing 140 and securing resilient seal member 142 between the components in sandwiched relation. As appreciated, first gimbal housing 138 may be sufficiently resilient to deflect upon insertion to permit mounting legs 144 to clear locking detents 148 and return to their initial position to engage the detents 148.

As mentioned hereinabove, seal member 142 of gimbal mount 104 is secured in interposed relation between first and second gimbal housings 138, 140. Seal member 142 preferably comprises a resilient center material (e.g., polyisoprene or natural rubber) with first and second layers of fabric 150,152 impregnated on the respective proximal and distal surfaces of the resilient center material. Fabric may be of any suitable fabric for example, a SPANDEX material containing about 20% LYCRA and about 80% NYLON available from Milliken. A suitable seal member or seal type is disclosed in commonly assigned U.S. patent application Ser. No. 09/449,368, filed Nov. 24, 1999, the contents of which are incorporated herein by reference. Seal member 142 defines central aperture 154 for sealed reception of a surgical instrument. In a preferred arrangement, first layer 150 is arranged to extend or overlap into aperture 154. In this manner, the fabric (which is stronger relative to the resilient material) is positioned to engage the surgical instrument upon passage through aperture 154 of seal member 142 thereby protecting the resilient material defining the aperture. This advantageously minimizes the potential of piercing, penetrating or tearing of the resilient material by the instrument. Alternatively, an additional layer of fabric on the proximal surface of seal member 142 may be superposed and arranged to drape within aperture 154 (not shown). Seal member 142 includes an annular depression 156 on its distal surface, i.e., within second layer 152 of fabric. Depression 156 receives ledge 158 of second gimbal housing 140 to facilitate fixation of seal member 142 between first and second gimbal housings 138, 140.

Figure 6:
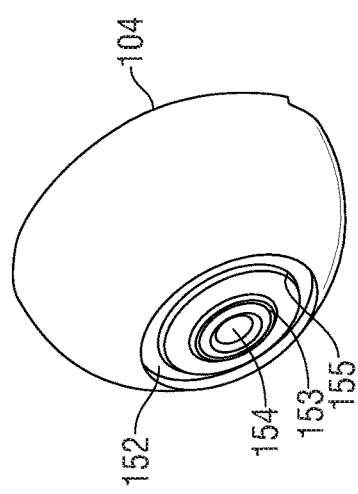
Figure 9:
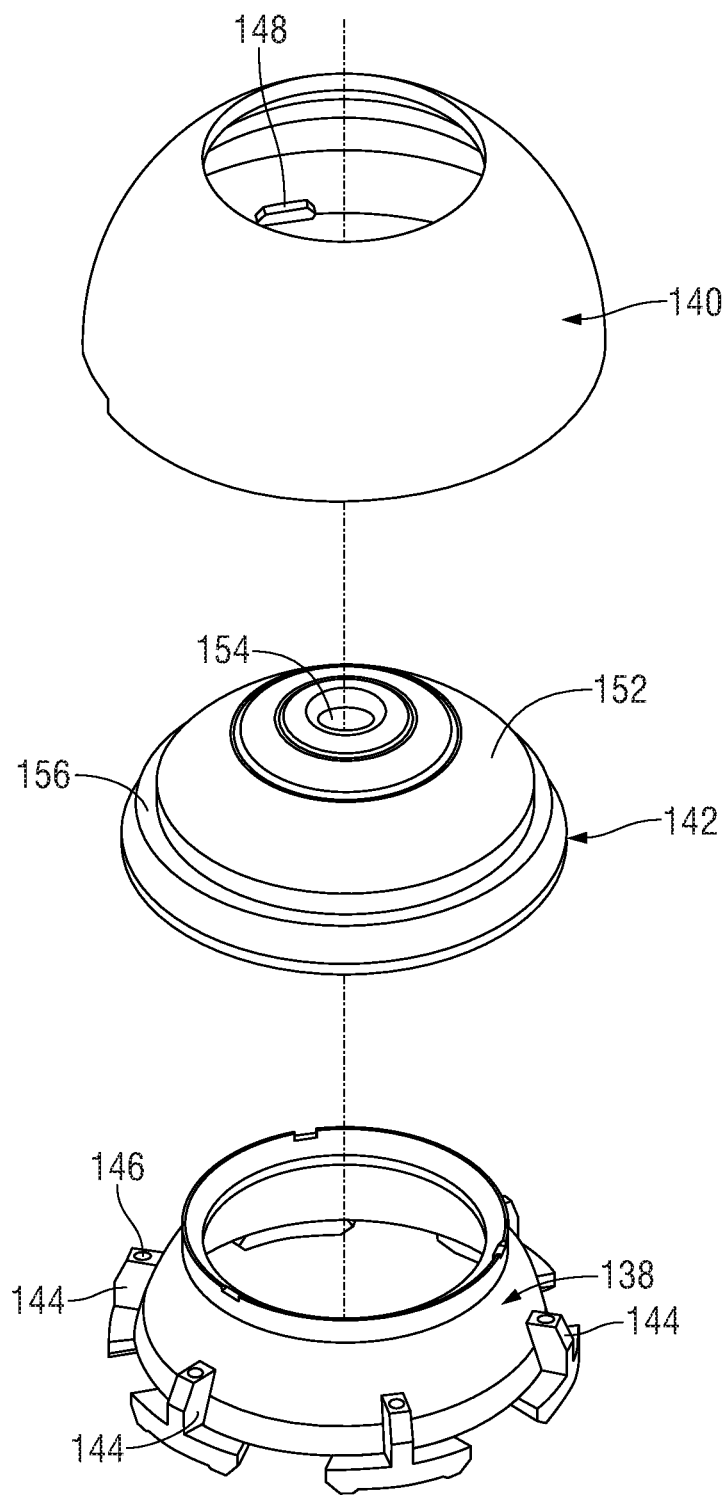
FIG. 9 is a perspective view illustrating the components of the gimbal mount.

Although seal member 142 is disclosed as an impregnated fabric arrangement, it is appreciated that other seal types may be used and still achieve the objectives of the present disclosure. Further, FIG. 6 illustrates annular depressions 153, 155 which have been pressed by a molding tool into layer 152. One or more similar depressions may be pressed into layer 150 to assist positioning of fabric during manufacture of seal member 142.

Figure 10:
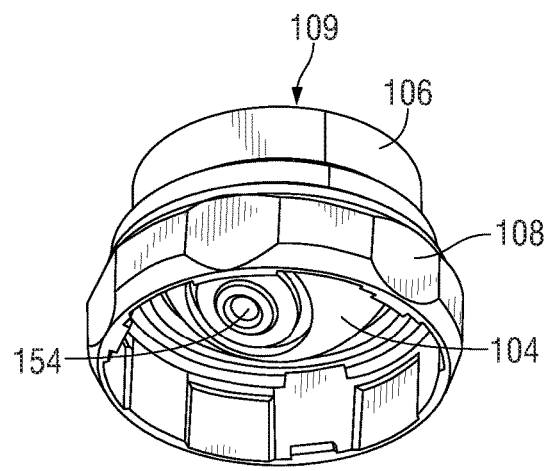
FIGS. 10-12 are perspective views illustrating the range of movement of the gimbal mount within the seal housing.
Figure 11:
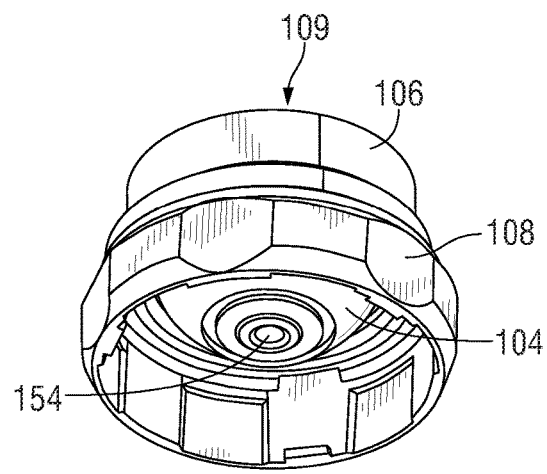
Figure 12:
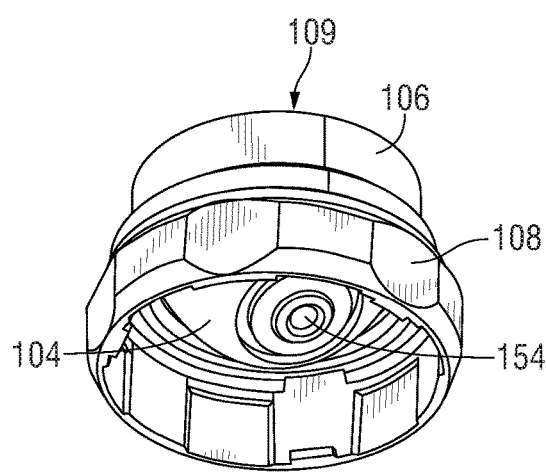

With reference now to FIGS. 10-12, in conjunction with FIG. 4, gimbal mount 104 is free to move within the annular space 134 defined between inner and outer walls 112,114 to permit angulation of the instrument relative to the seal axis "b" while still maintaining a seal thereabout. Specifically, gimbal mount 104 is adapted for swiveling movement about a center of rotation "c" which is coincident with the axis of seal assembly 100. In this regard, the axis of the aperture 154 of seal member 142 intersects the axis "b" of the seal assembly 100 during angulation of the instrument. During angulation, gimbal mount 104 is only in contact with seal housing 102 along distal arcuate surface 118 of proximal housing 106 as well as along skirt seal 132. Specifically, the arcuate inner surface of first gimbal housing 138 rides along distal arcuate surface 118 of inner wall 112 in contacting relation therewith (under the bearing influence of skirt seal 132) to permit gimbal mount 104 to swivel within seal housing 102. Preferably, there is no other contact of gimbal mount 104 with any of the other components of seal housing, which thereby substantially minimizes resistance to the angulating movement. A lubricant may be provided between distal arcuate surface 118 and the inner surface of first gimbal housing 138 to facilitate angulation.

In a preferred arrangement, gimbal mount 104 may angulate or rotate through an angle inclusive of about 25 degrees, more preferably about 22.5 degrees, relative to seal axis "b". Annular stop 136 may further restrict angulation by a couple of degrees of movement to be inclusive of an angle of about 19 degrees relative to axis "b".

Seal assembly 100 may be associated with, or joined to, cannula assembly 200 in a variety of ways. In a preferred embodiment, seal housing 102 of seal assembly 100 and cannula housing 204 of cannula assembly 200 are adapted to detachably engage each other, e.g., through a bayonet lock or like mechanical means. As previously discussed, proximal and distal housing components 106, 108 may define an upper housing component 109 which is mountable directly to cannula assembly 200. Alternatively, inner housing portion 110 which defines a lower housing component may be directly mounted to cannula assembly 200 independent of the upper housing component 109. Specifically, the lower housing component 110 which houses gimbal mount 104 may be mounted to cannula assembly independent of the remaining housing components. The upper housing may then be mounted to lower housing or cannula assembly 200 as needed. Even further, upper housing component 109 may be mounted to cannula assembly 200 without lower housing component 110. Other means of joining seal assembly 100 to cannula assembly 200 will be readily apparent to one of ordinary skill in the art.

Figure 13:
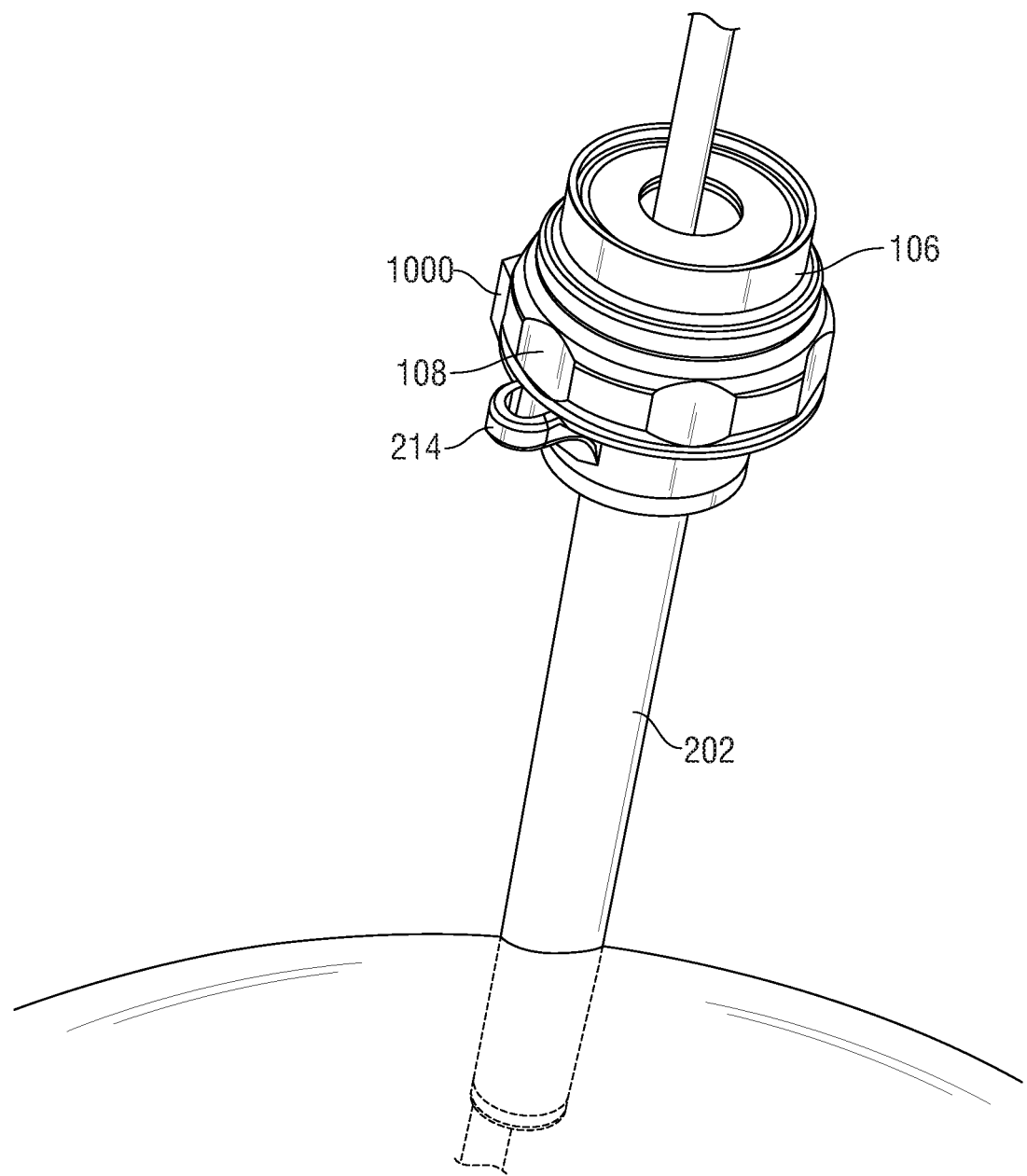
FIG. 13 is a view illustrating the cannula assembly and seal assembly accessing an internal cavity with an instrument introduced therein.
Figure 14:
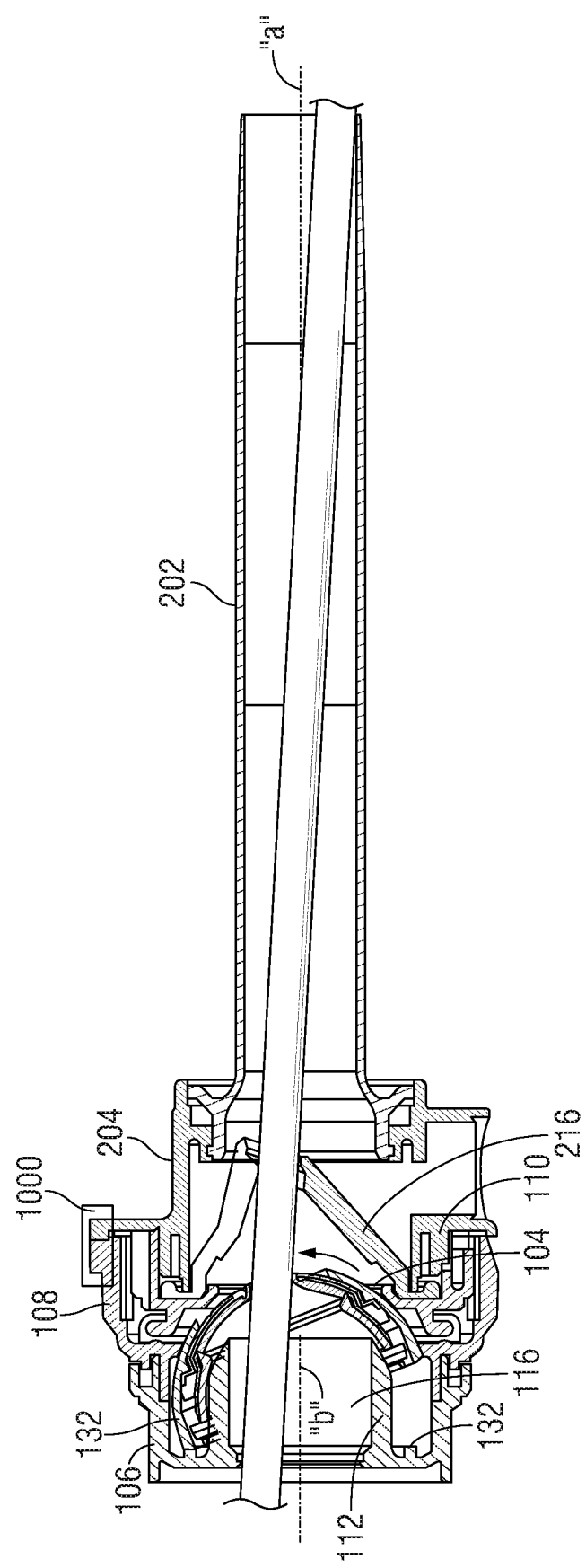
FIG. 14 is a side cross-sectional view of the cannula and seal assemblies illustrating a range of movement of the surgical instrument.

Referring now to FIGS. 13-14, use of the seal assembly 100 and cannula assembly 200 in connection with introduction of a surgical instrument will be discussed. Seal assembly 100 is mounted to cannula assembly 200 which is previously introduced into an insufflated abdominal cavity. An instrument is inserted into seal assembly 100 through passage 116 of inner cylindrical guide wall 112 in seal housing 102. If the axis of the instrument is not perfectly aligned with the axis "a" of cannula assembly 200 or axis "b" of seal assembly 100, then the surgical instrument will contact the inner guide wall 112 and/or the inner surface of seal member 142. Contact with the seal member 142 can cause some deformation of the seal member 142. The instrument slides along the surface of the gimbal mount 104 and/or the seal member 142, to the aperture 154. Aperture 154 stretches to accommodate the instrument diameter, as necessary. The instrument passes further distally into the cannula housing 204 passing through duckbill valve 216 and cannula sleeve 202 into the body cavity. Once the instrument is disposed within the aperture 154, and the friction at the skirt seal 132, gimbal mount 104 and arcuate surface 118 is overcome, gimbal mount 104 swivels with respect to seal housing 102 as the instrument is manipulated. The gimbal mount 104 is free to swivel relative to housing 102, while allowing seal member 142 to maintain sealing engagement with the instrument passed therethrough, as well as maintaining the seal around the gimbal mount 104. Preferably, the seal member 142 includes resilient material and fabric material which resists deformation of the aperture 154, as well as tearing of the seal member 142.

As previously mentioned, by providing a selectively actuatable mechanism that i) when unactuated, prevents a rotatably connectable upper housing portion of a seal housing from inadvertently rotating relative to a lower housing portion of the seal housing during use, and that ii) when actuated, enables a user to rotate and thereby disconnect the upper housing portion from lower housing portion of the seal housing, various advantages may be achieved. For example, by enabling a user to rotate and thereby disconnect the upper housing portion from lower housing portion of the seal housing, one advantage that may be achieved is that a specimen may be removed from a surgical site through the lower housing portion (typically through a duckbill or other type of zero seal valve located therein) and without the need to pull the specimen through the upper housing portion (which typically would require pulling the specimen through a more restrictive instrument seal located therein).

Another advantage that may be achieved by providing a selectively actuatable mechanism of the type described herein is that inadvertent rotation of the upper housing portion relative to the lower housing portion may be prevented. Such inadvertent rotation of the upper housing portion relative to the lower housing portion may be particularly important in embodiments in which the obturator assembly (not shown) is bladeless, since it is often the case that bladeless obturators are "clocked" (inserted using a back-and-forth twisting motion while simultaneously providing a distal force) in order to facilitate entry through tissue layers and into the body. This clocking motion may increase the likelihood for inadvertent rotation, and thus inadvertent disconnection, of the upper housing portion 109 relative to the lower housing portion 110. Of course, these twisting forces may also occur when a bladed, e.g., sharp, obturator assembly is employed, and thus the present invention, in accordance with various embodiments thereof, is also applicable to embodiments that employ a bladed obturator assembly.

Another advantage that may be achieved by providing a selectively actuatable mechanism of the type described herein is that it may reduce the amount of rotation needed in order to connect the upper housing portion relative to the lower housing portion. Various existing rotatable valve housing connection arrangements (e.g., existing valve housing connection arrangements that employ a bayonet type connection between the upper housing portion and the lower housing portion, typically requires that the upper housing portion be rotated a quarter turn, e.g., 90 degrees, relative to the lower housing portion. By providing a rotation prevention mechanism, such as rotation prevention mechanism 1000 shown in the example embodiments of FIGS. 15-17, the amount of rotation needed for connecting the upper housing portion and the lower housing portion may be reduced so as to be smaller than a quarter turn. This reduction in the amount of rotation needed in order to connect the upper housing portion and the lower housing portion may make it easier for a user, e.g., a surgeon, to remove the upper housing portion from the lower housing portion during surgery, especially if the surgeon desires to, or is only able to, use a single hand to do so, as is often the case in complicated surgical procedures.

Making it easier for a user, e.g., a surgeon, to remove the upper housing portion from the lower housing portion during surgery, particularly if a surgeon uses a single hand to do so, is also an advantage that is provided by various ones of the example embodiments disclosed hereinabove. For example, the distal movement of the finger 1003 that is employed in order to disconnect the upper housing portion 109 from the lower housing portion 110 is relatively easy for a user to perform, especially when the user has only a single hand to do so. The user can exert a distal force on the finger 1003 with the user's finger of the hand that is already gripping the cannula, thereby potentially obviating the need for the user to use a second hand (which might be engaged in performing other aspects of the surgical procedure).

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

What is claimed is:

1. A surgical access device comprising:
    a seal assembly including an upper housing portion having a first seal and a lower housing portion including a second seal, the first seal supported by a seal mount disposed in the upper housing portion, the seal mount having a first housing and a second housing, the first housing rotatable relative to the second housing to secure the first seal between the first and second housings of the seal mount, the upper housing portion being rotatably connectable to the lower housing portion; and
    a mechanism configured to prevent inadvertent relative rotation of, and disconnection of, the upper housing portion and the lower housing portion, the mechanism further configured to be selectively actuated by a user, such that, when actuated, the upper housing portion is selectively rotatable relative to, and disconnectable from, the lower housing portion.

2. The surgical access device of claim 1, wherein the mechanism includes components that are integrally formed with one or both of the upper housing portion and the lower housing portion.

3. The surgical access device of claim 1, wherein the mechanism includes components that are integrally formed with other components that are fixedly connected to one or both of the upper housing portion and the lower housing portion.

4. The surgical access device of claim 1, wherein the mechanism includes a first component that is integrally formed with the upper housing portion and a second component that is fixedly connected to the lower housing portion.

5. The surgical access device of claim 4, wherein the first component comprises a finger.

6. The surgical access device of claim 5, wherein the finger is integrally formed with a circumferential edge of a main housing, the main housing fixedly connected to the lower housing portion.

7. The surgical access device of claim 6, wherein the finger includes a ramp located on its upper surface.

8. The surgical access device of claim 7, wherein the second component of the mechanism includes a protrusion.

9. The surgical access device of claim 8, wherein the protrusion is integrally formed with a circumferential edge of the upper housing portion.

10. The surgical access device of claim 8, wherein the protrusion includes a distally-extending member.

11. The surgical access device of claim 6, wherein the finger is configured for resilient movement relative to the main housing about its point of attachment thereto, such that at least a portion of the finger is moveable distally relative to the main housing.

12. The surgical access device of claim 10, wherein, as the upper housing portion of the seal assembly is rotated in a first direction, the distally-extending member of the protrusion travels up a sloping surface of the ramp and exerts a force on the finger sufficient to cause the finger to move distally relative to the main housing until, when the distally-extending member of the protrusion reaches an end of the sloping surface of the ramp, the force exerted on the ramp by the distally-extending member of the protrusion is removed, and the finger, by virtue of its resilience, is allowed to move proximally to a position in which the distally-extending member of the protrusion is distal relative to an uppermost point of the ramp, thereby preventing the upper housing portion from rotation in a second direction opposite to the first direction.

13. The surgical access device of claim 12, wherein, upon a user exerting a force on the finger, the finger is moveable distally relative to the main housing until the uppermost point of the ramp is located distal relative to the distally-extending member of the protrusion such that the upper housing portion of the seal assembly is not prevented from rotation, but rather is free to rotate, in the second direction relative to the lower housing portion.

14. A surgical access device comprising:
    a seal assembly including an upper housing portion having a first seal and a lower housing portion including a second seal, the first seal having a gimbal housing, the upper housing portion being rotatably connectable to the lower housing portion; and
    a mechanism configured to prevent inadvertent relative rotation of, and disconnection of, the upper housing portion and the lower housing portion, the mechanism further configured to be selectively actuated by a user, such that, when actuated, the upper housing portion is selectively rotatable relative to, and disconnectable from, the lower housing portion.

15. The surgical access device of claim 14, wherein the gimbal housing includes a first gimbal housing and a second gimbal housing.

16. The surgical access device of claim 15, wherein the first gimbal housing has a plurality of mounting legs radially spaced around a periphery of the first gimbal housing.

17. The surgical access device of claim 16, wherein the second gimbal housing has locking detents for engaging the mounting legs.

* * * * *